(12) United States Patent
Knight et al.

(10) Patent No.: US 11,261,415 B2
(45) Date of Patent: *Mar. 1, 2022

(54) REACTOR SYSTEMS

(71) Applicant: ABEC, Inc., Bethlehem, PA (US)

(72) Inventors: Cameron Knight, Springfield, MO (US); Todd Jones, New Tripoli, PA (US); Brady Cole, Center Valley, PA (US); Paul Kubera, Schnecksville, PA (US); Cindy L. Donovan, Allentown, PA (US)

(73) Assignee: ABEC, INC., Bethlehem, PA (US)

( * ) Notice: Subject to any disclaimer, the term of this patent is extended or adjusted under 35 U.S.C. 154(b) by 117 days.

This patent is subject to a terminal disclaimer.

(21) Appl. No.: 16/231,663

(22) Filed: Dec. 24, 2018

(65) Prior Publication Data

US 2019/0203166 A1    Jul. 4, 2019

Related U.S. Application Data

(63) Continuation of application No. 15/252,273, filed on Aug. 31, 2016, now abandoned, which is a (Continued)

(51) Int. Cl.
*C12M 1/00* (2006.01)
*B01J 19/00* (2006.01)
(Continued)

(52) U.S. Cl.
CPC ......... *C12M 23/52* (2013.01); *B01F 7/00133* (2013.01); *B01F 7/00141* (2013.01); *B01F 7/1605* (2013.01); *B01F 7/186* (2013.01); *B01F 13/0032* (2013.01); *B01F 15/00006* (2013.01); *B01F 15/0085* (2013.01); *B01F 15/00785* (2013.01); *B01F 15/00896* (2013.01); *B01F 15/065* (2013.01); *B01J 19/0066* (2013.01); *B01J 19/18* (2013.01); *B01J 19/1812* (2013.01); *B01J 19/24* (2013.01); *C12M 23/28* (2013.01); *C12M 23/46* (2013.01); *C12M 23/48* (2013.01); *C12M 27/02* (2013.01); *B01J 2219/00094* (2013.01); *B01J 2219/00768* (2013.01); *B01J 2219/1943* (2013.01); *B01J 2219/24* (2013.01)

(58) Field of Classification Search
None
See application file for complete search history.

(56) References Cited

U.S. PATENT DOCUMENTS 4,932,533 A    6/1990   Collier
5,525,512 A    6/1996   Piler et al.
(Continued)

FOREIGN PATENT DOCUMENTS

| EP | 1854871 A1 | 11/2007 |
|---|---|---|
| WO | 2005104706 A2 | 11/2005 |
| WO | 2008040568 A1 | 4/2008 |
| WO | 2012125730 | 9/2012 |

*Primary Examiner* — William H. Beisner
(74) *Attorney, Agent, or Firm* — Patrick J. Halloran

(57) ABSTRACT

This disclosure relates to equipment utilized to manufacture chemical agents, particularly biopharmaceuticals. In some embodiments, reactor systems comprising a mobile carriage assembly; a disposable reaction container removably attached to the carriage assembly; and, a carriage holder into which the mobile carriage assembly may be removably inserted are provided.

22 Claims, 4 Drawing Sheets

Related U.S. Application Data continuation of application No. 14/969,937, filed on Dec. 15, 2015, now abandoned, which is a continuation of application No. 13/420,338, filed on Mar. 14, 2012, now Pat. No. 9,228,165.

(60) Provisional application No. 61/453,099, filed on Mar. 15, 2011.

(51) Int. Cl.
  *B01J 19/18* (2006.01)
  *C12M 1/06* (2006.01)
  *B01F 7/00* (2006.01)
  *B01F 7/16* (2006.01)
  *B01F 7/18* (2006.01)
  *B01F 13/00* (2006.01)
  *B01F 15/00* (2006.01)
  *B01F 15/06* (2006.01)
  *B01J 19/24* (2006.01)
  *C12M 3/00* (2006.01)

(56) References Cited

U.S. PATENT DOCUMENTS

| | | |
|---|---|---|
| 5,547,329 A | 8/1996 | Hirai et al. |
| 6,867,393 B1 | 3/2005 | Lewis |
| 7,682,823 B1 | 2/2010 | Runyon |
| 7,815,851 B1 | 10/2010 | Lewis |
| 8,381,780 B2 | 2/2013 | Fisher et al. |
| 9,228,165 B2 | 1/2016 | Knight |
| 2003/0219453 A1 | 11/2003 | Maisonneuve et al. |
| 2004/0190372 A1 | 9/2004 | Goodwin et al. |
| 2006/0280028 A1 | 12/2006 | West et al. |
| 2008/0139865 A1 | 6/2008 | Galliher et al. |
| 2008/0145924 A1 | 6/2008 | Kobayashi et al. |
| 2008/0206847 A1 | 8/2008 | Kunas et al. |
| 2009/0111179 A1 | 4/2009 | Hata et al. |
| 2009/0180933 A1 | 7/2009 | Kauling et al. |
| 2009/0290962 A1 | 11/2009 | Fisher et al. |
| 2010/0062522 A1 | 3/2010 | Fanning et al. |
| 2010/0149908 A1 | 6/2010 | Singh et al. |
| 2010/0301042 A1 | 12/2010 | Kahlert |
| 2011/0059523 A1 | 3/2011 | Knight |
| 2012/0100605 A1 | 4/2012 | Kauling et al. |

1a / 1b: mobility implement (wheels, skid, track)
2: accessory implements (e.g., agitator)
3: carriage platform

ISOMETRIC VIEW
(CARRIAGE ASSEMBLY)

ISOMETRIC VIEW
(CARRIAGE ASSEMBLY)

1a, 1b: mobility implements (wheels, skid, track, etc.)
2: accessory features
3: platform
4: container reversibly, fixably attached to platform 1a: wheels
1b: wheels / tracks for loading using tracks 8
5: carriage
6: holder (external jacket system)
7: holder door
8: holder tracks (for insertion of carriage)

ISOMETRIC VIEW
(ASSEMBLED POSITION)

REACTOR SYSTEMS

RELATED APPLICATIONS

This application is a continuation application of U.S. Ser. No. 15/252,273 filed on Aug. 31, 2016, now abandoned which is a continuation application of U.S. Ser. No. 14/969,937 filed on Dec. 15, 2015, now abandoned, which is a continuation application of U.S. Ser. No. 13/420,338 filed on Mar. 14, 2012, now U.S. Pat. No. 9,228,165 B2, which claims priority to U.S. Ser. No. 61/453,099 filed Mar. 15, 2011.

FIELD OF DISCLOSURE

This disclosure relates to equipment utilized to manufacture chemical agents, particularly biopharmaceuticals.

BACKGROUND INFORMATION

This disclosure relates to equipment having reaction vessels used to manufacture chemical and/or biological products such as biopharmaceuticals. For instance, fermenters commonly provide a reaction vessel for cultivation of microbial organisms or mammalian, insect, or plant cells to produce such products. Currently available systems do not provide for simple removal of the components of a reaction from a reaction container and cleaning of equipment after a reaction is completed. The systems described herein solve these problems by providing a custom geometry, and optionally a sterile container used for reactions (e.g., biological, chemical), that does not require cleaning and re-sterilization after use is solved by the system described herein. The system also provides for ease of use in loading and unloading the disposable reaction container from a holder (e.g., an external jacket system).

SUMMARY OF THE DISCLOSURE

The systems described herein provide a mobile single-use disposable reaction container that may be housed within a holding system (e.g., external jacket system). In some embodiments, reactor systems comprising a mobile carriage assembly; a disposable reaction container removably attached to the carriage assembly; and, a carriage holder into which the mobile carriage assembly may be removably inserted are provided. In certain embodiments, the carriage holder comprises a heat transfer jacket. The mobile carriage may optionally comprise at least one implement selected from the group consisting of at least one wheel or track, an implement providing for fixably attaching the disposable reaction container to the carriage, an implement providing for fixably attaching the carriage to the holder, and an implement for mixing the components of the reaction. The implement for mixing the components of the reaction may be, for example, an agitator that optionally comprises a shaft and impeller that is incorporated in the reaction container and that connects to a drive mechanism fixably attached to the carriage. The disposable reaction container may comprise a sterile, sealable interior chamber in which reaction components may be reacted with one another; may be reversibly fixably attached to the mobile carriage assembly; may be removed from the mobile carriage assembly after the reaction is complete; may separate the contents of the reaction from the external environment after removal from the mobile carriage assembly; and/or, incorporate a sparge or other accessory. In certain embodiments, the holder may comprise a receiving implement with which the carriage may be inserted into and optionally affixed to the holder; maintain the desired geometry of the disposable reaction container, optionally including reaction container anti-swirl baffles; provide for heating and/or cooling of the reaction components within the reaction container; comprise a door for maintaining the reaction container separated from the exterior of the holder; and/or, comprise one or more anti-swirl and/or heat exchange baffles. In some embodiments, the receiving implement comprises one or more wheels or tracks. Other features of these reactor systems will be apparent from the description provided herein including, for example, FIGS. 1-4. Thus, in some embodiments, the reactor systems may comprise:

1) a mobile carriage assembly;
2) a disposable reaction container removably attached to the carriage assembly; and,
3) a holder with a heat transfer jacket (e.g., external jacket system) comprising an opening into which the carriage (e.g., and reaction container) may be removably inserted;

wherein:
  a) the mobile carriage assembly optionally comprises [at least one of]:
    i. at least one implement providing mobility to the carriage, such as one or more wheels or tracks;
    ii. at least one implement providing for fixably attaching the disposable reaction container to the carriage; and,
    iii. at least one implement providing for fixably attaching the carriage to the holder;
    iv. one or more implements such as an agitator that optionally comprises a shaft and impellar fixably attached to the carriage and providing for mixing of the contents of the reaction within the reaction container;
  b) the disposable reaction container:
    i. provides a sterile, sealable interior chamber in which reaction components may be reacted with one another;
    ii. may be reversibly fixably attached to the carriage such that one or more of the implements of the carriage may be coupled to the reaction container (e.g., agitator (e.g., the shaft and impellar being affixed to a motor on the carriage and providing for mixing of the contents of the reaction within the reaction container)) while others may be positioned outside the reaction container (e.g., the baffle(s)) and/or other components of the system);
    iii. may be removed from the carriage after the reaction is complete, optionally keeping the contents of the reaction separated from the external environment (e.g., under sterile conditions); and,
    iv. optionally comprises a sparge (e.g., gas introduction device); and,
  c) the holder [may]:
    i. comprises an receiving implement (e.g., one or more tracks) with which the carriage may be inserted into and optionally affixed to the holder;
    ii. maintains the desired geometry (e.g., shape) of the disposable reaction container, optionally including reaction container anti-swirl baffles;
    iii. provides for heating and/or cooling of the reaction components within the reaction container;

iv. comprises a door for maintaining the carriage and reaction container separated from the exterior of the holder (e.g., locking the carriage/reaction container within the holder); and, v. optionally comprises one or more anti-swirl and/or heat exchange baffle(s).

In some embodiments, a mobile carriage assembly to which a disposable reaction container may be removably attached, the mobile carriage assembly comprising at least one wheel and/or track Sand an implement for mixing the components of the reaction in the reaction chamber, is provided. Exemplary of such embodiments may be those shown in FIGS. 1 and 2. Such a mobile carriage assembly may be placed into a holder as, for example, described herein to carry out a reaction within the disposable reaction container (FIG. 3).

The reactor systems described herein may be used to carry out any of a variety of reactions, such as a chemical process, a pharmaceutical process, and/or a biological process (or combinations thereof). Exemplary biological processes may include, for example, microbiological culture, mammalian cell culture, and plant cell culture. In some embodiments, the reaction may be may be use in at least one step of a process for the production of a composition comprising a peptide, protein, nucleic acid, complex thereof, combination thereof, or the like for use in, for example, for the prevention and/or treatment of a disease (e.g., as a vaccine). Also provided are methods for carrying out such reactions using the reactor systems described herein. The products of such reactions are also provided by this disclosure. Additional embodiments and advantages of these systems are described below.

DETAILED DESCRIPTION

Figure 1:
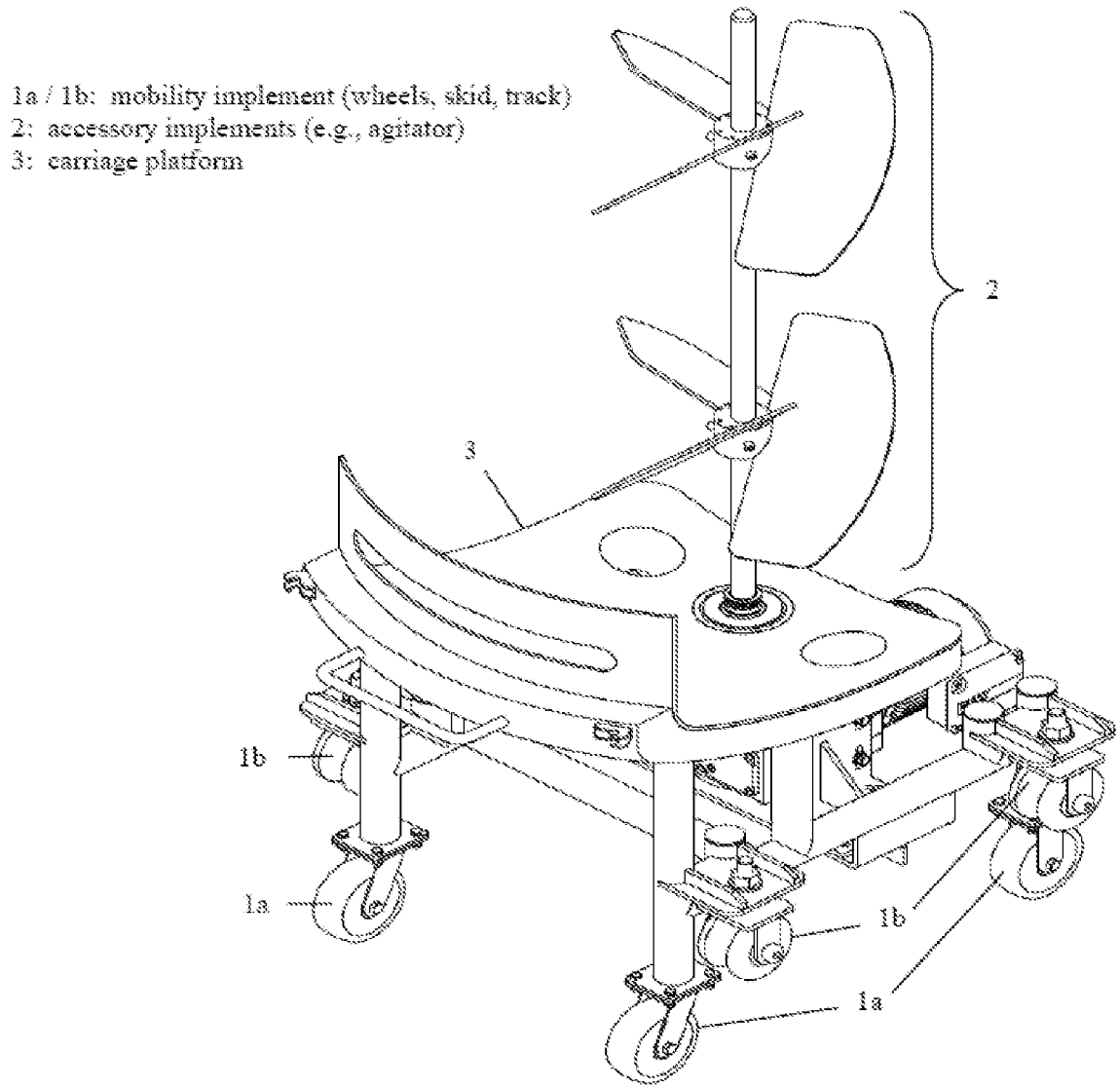
FIG. 1. Exemplary carriage assembly.

The systems described herein provide a mobile single-use disposable reaction container that may be housed within a holding system (e.g., external jacket system). These systems are fully customizable in terms of the types and size of reactions that may be performed therein. The reaction systems may be designed to accommodate nearly any size reaction by coordinating the size of the various components relative to one another such that the required attachments may be made and various reaction conditions supported. The types of reactions may also vary as the components may be made of any suitable material required to withstand the reaction conditions (e.g., types of reactants, heat, pressure, etc.) In some embodiments, the system comprises a mobile carriage assembly, a disposable reaction container removably attached to the mobile carriage assembly; and, a holder with a heat transfer jacket (e.g., external jacket system) comprising an opening into which the mobile carriage assembly (e.g., and reaction container) may be removably inserted. In some embodiments, the holder may not comprise a heat transfer jacket. The mobile carriage assembly optionally comprises at least one implement providing mobility to the carriage, such as one or more wheels and/or tracks; at least one implement providing for fixably attaching the disposable reaction container to the mobile carriage assembly; and, at least one implement providing for fixably attaching the mobile carriage assembly to the holder; and/or one or more implements such as an agitator that optionally comprises a shaft and impellar fixably attached to the mobile carriage assembly and providing for mixing of the contents of the reaction within the reaction container. The disposable reaction container may comprise a sterile, sealable, interior chamber in which reaction components may be reacted with one another; may be reversibly fixably attached to the mobile carriage assembly such that one or more of the implements of the mobile carriage assembly may be coupled to the reaction container (e.g., agitator (e.g., the shaft and impellar being affixed to a motor on the mobile carriage assembly and providing for mixing of the contents of the reaction within the reaction container)) while others may be positioned outside the reaction container (e.g., the baffle(s)) and/or other components of the system); may be removed from the mobile carriage assembly after the reaction is complete, optionally keeping the contents of the reaction separated from the external environment (e.g., under sterile conditions); and/or optionally comprises a sparge (e.g., gas introduction device). The holder may comprise a receiving implement (e.g., one or more tracks) with which the mobile carriage assembly may be inserted into and optionally affixed to the holder; may maintain the desired geometry (e.g., shape) of the disposable reaction container, optionally including reaction container anti-swirl baffles; may provide for heating and/or cooling of the reaction components within the reaction container; comprises a door for maintaining the mobile carriage assembly and reaction container separated from the exterior of the holder (e.g., locking the carriage/reaction container within the holder); and/or comprises one or more anti-swirl and/or heat exchange baffle(s). The reactor system may be used to carry out reaction involving, for example, a chemical process, a pharmaceutical process, and a biological process. For instance, a biological process may be a microbiological culture, mammalian cell culture, and plant cell culture. In some embodiments, the reaction may be use in at least one step of a process for the production of a composition comprising a peptide, protein, nucleic acid, complex thereof, combination thereof, or the like for use in, for example, for the prevention and/or treatment of a disease (e.g., as a vaccine). Methods for carrying out these reactions are also provided. It is noted that the terms "attached", "fixably attached", "affixed", and/or "adjoined" mean that at least two materials are linked or bonded to one another in a temporary or permanent (or substantially permanent) manner. And parts are "reversibly" attached where one part may be attached and detached from another part. For example, one of ordinary skill in the art would understand that the at least one implement providing for fixably attaching the disposable reaction container to the mobile carriage assembly may also provide for removal of the disposable reaction container from the carriage. Similarly, the at least one implement providing for fixably attaching the mobile carriage assembly to the holder may also provide for removal of the mobile carriage assembly from the holder. The mobile carriage assembly and diposable reaction container may be of any suitable size, as long as the components are compatible with one another.

FIG. 1 illustrates an exemplary mobile carriage assembly. As briefly described above, the mobile carriage assembly may comprise a mobility implement, such as wheels (1) or tracks. The mobile carriage assembly may also comprise a set of primary and secondary mobility implements (1a, 1b). The primary mobility implements (1a) may be used, for example, to move (e.g., roll) the mobile carriage assembly. The secondary mobility implements (1b) may be used to insert/attach and/or remove the mobile carriage assembly into or from, respectively, the holder (e.g., 8 in FIG. 3). The mobile carriage assembly may also include a platform (3) and one or more additional implements such as an agitator (2). As mentioned above, the shaft/impellar assembly may be affixed to a motor on the mobile carriage assembly. The motor may also be found elsewhere (e.g., not affixed to the carriage) as long as it is capable of powering the shaft/impellar assembly such that the reaction components may be mixed.

Figure 2:
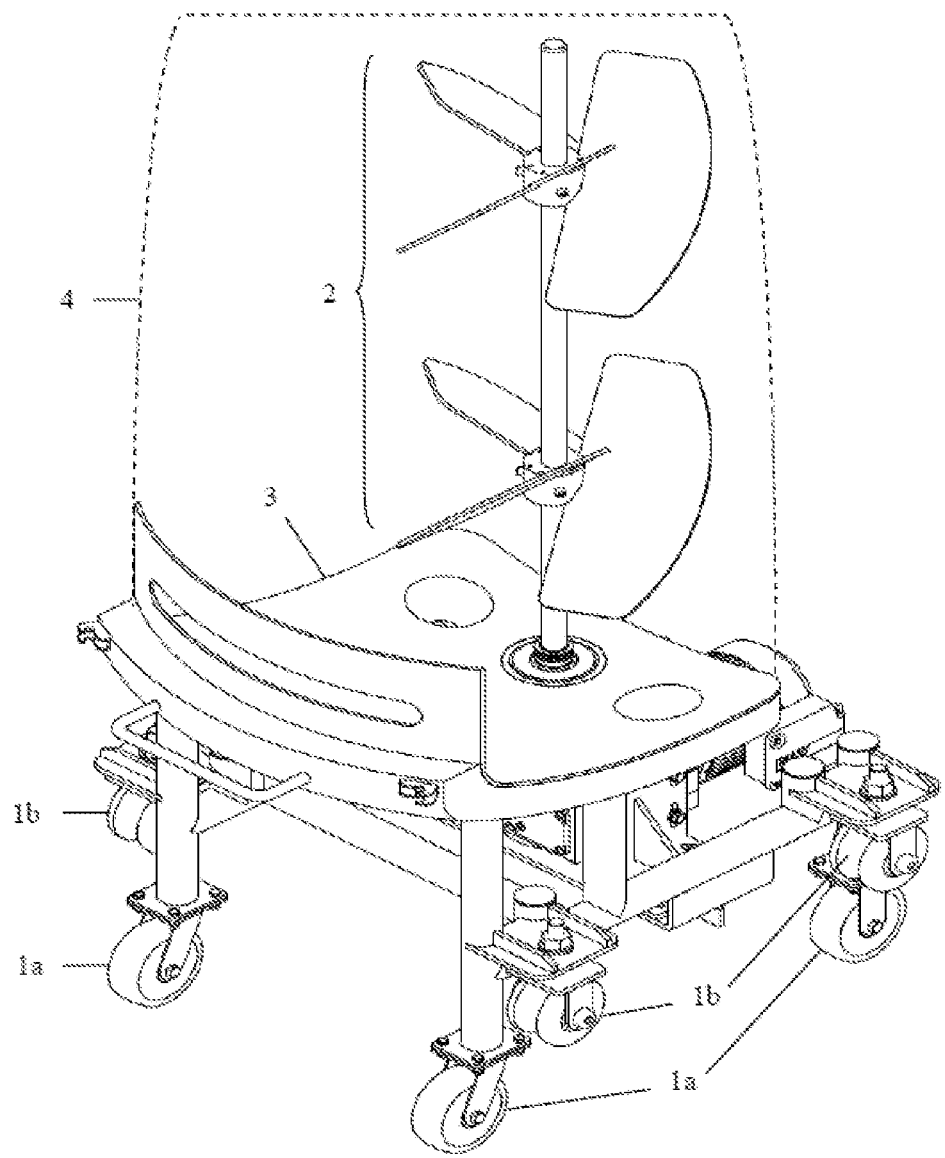
FIG. 2. Exemplary carriage assembly with reversibly attached reaction container (4).
Figure 3:
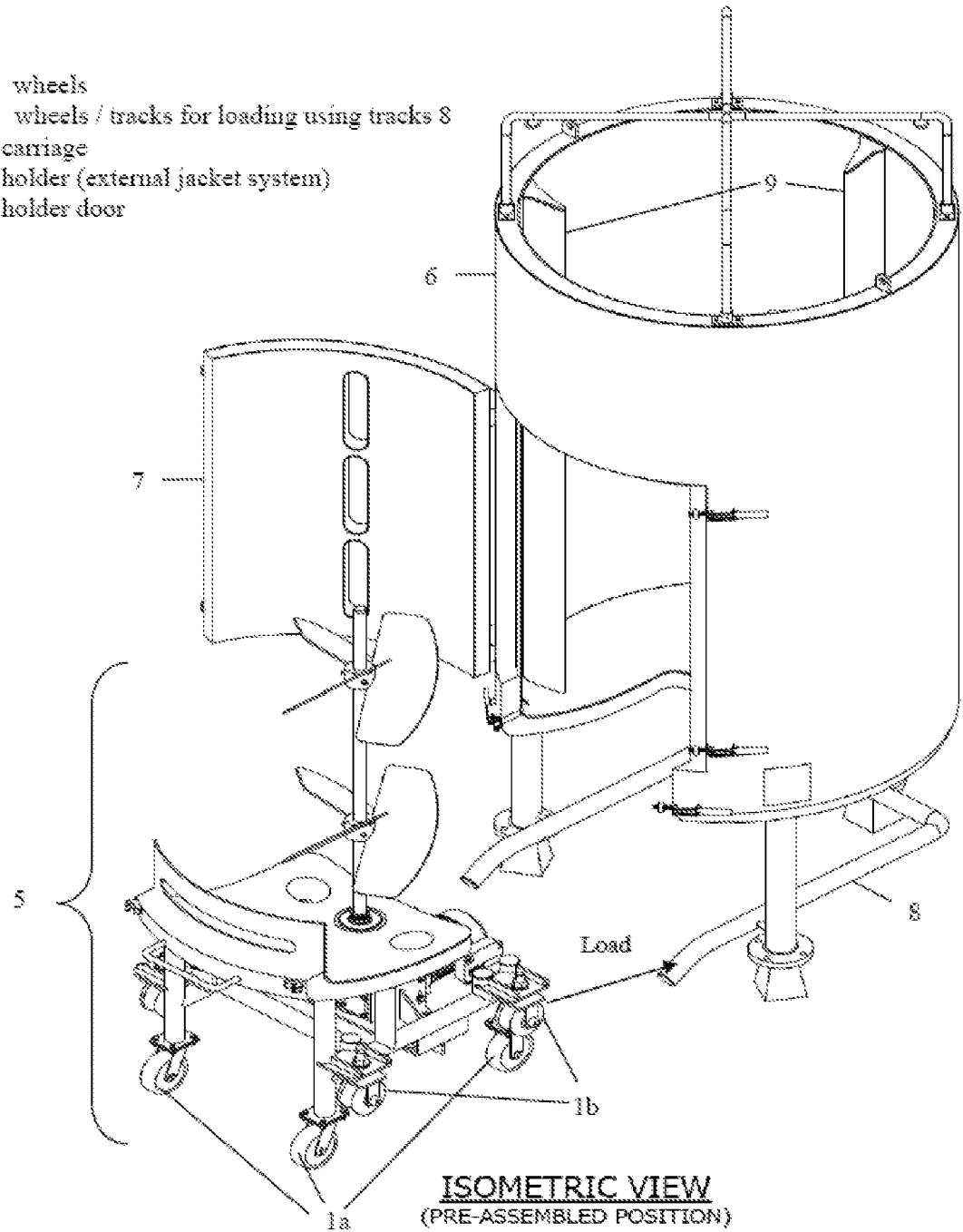
FIG. 3. Exemplary carriage assembly and holder (e.g., external jacket system) and exemplary tracks (8) for reversibly inserting carriage assembly (optionally also comprising reaction container) into holder.

As shown in FIG. 2, the reaction container (4) in which the reaction is carried out may be attached to the platform (3). The reaction container may be reversibly affixed to the platform so that it may be attached before the reaction takes place and removed after the reaction is complete. The reaction containers may be made from a polymer film, typically as a monolayer "sandwich" of a product contact layer (e.g., typically low-density polyethylene), a gas barrier layer (e.g., ethyl vinyl acetate), and a strength layer. Film sheets may be welded together to form the desired reaction container shape; access ports for material additions/withdrawals, instruments, agitator(s), etc., may be also welded in place. Access ports are typically sealed as appropriate. For sterile reactions, the completed reaction container assembly may be sterilized before use by, for example, exposure to gamma-irradiation. The reaction container assembly (e.g., mobile carriage assembly with fixably, reversibly attached reaction container) may be loaded into a holder before use (e.g., as shown in FIG. 3 using wheel/track assembly 1b and track 8), and properly positioned/secured. The agitator drive attachment and sterile connections are typically then made via tube welding using the appropriate connectors, etc. before charging the reaction container with the reaction components (e.g., sterile media) and/or, for biological reactions, inoculation.

Figure 4:
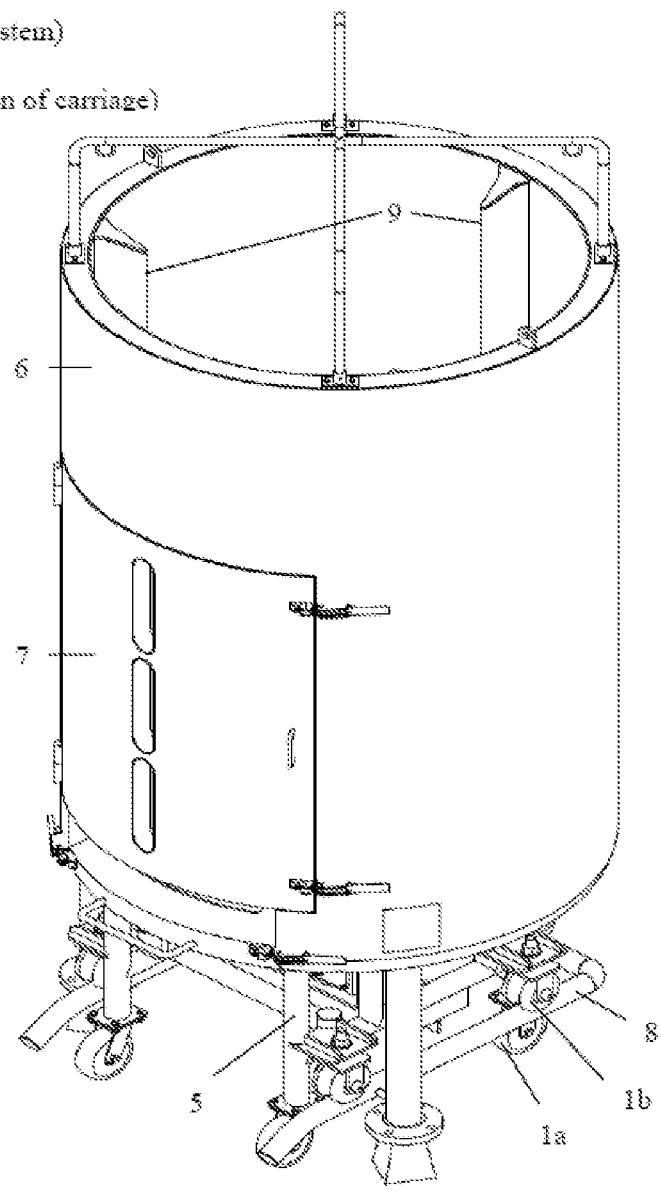
FIG. 4. Exemplary reactor system in which carriage assembly is contained within holder and separated from exterior by door (7).

FIG. 3 illustrates another view of an exemplary reactor system in which the mobile carriage assembly (5) may be loaded onto (or inserted into) the holder (6). As briefly mentioned above, the mobile carriage assembly may be loaded onto (or inserted into) holder (6) using wheel/track assembly made up of wheel 1b and track 8. The mobile carriage assembly may also be removed from the holder using the wheel/track assembly. Wheels 1a may or may not remain in contact with the ground once the mobile carriage assembly is loaded onto (or inserted into) holder (6). The reaction container may be fixably reversibly attached to the mobile carriage assembly (e.g., to platform (3)) prior to loading or inserting of assembly into the holder. The reaction container may also be attached to the mobile carriage assembly after the mobile carriage assembly has been loaded onto (or inserted into) the holder (6). For example, the reaction container may be loaded into the holder (6) from the open top thereof and rested upon (e.g., reversibly fixably attached) the mobile carriage assembly (5). Holder (6) may contain one or more heat transfer (e.g., heat exchange) and/or anti-swirl baffles (9). FIG. 4 illustrates a closed system in which the mobile carriage assembly (e.g. (5) as shown in FIG. 3) is contained within holder (6) using a door (7) or other suitable implement. These systems may also include a cover device to restrain the top of the reaction container (e.g., attached to the holder, such as a lid), thus allowing operation at higher pressure to improve the driving force for oxygen transfer, thus improving process performance.

The holder (e.g., 6 in FIG. 4) may be of any suitable format. For instance, while a door (e.g., 7 in FIG. 4) may be used to contain the mobile carriage assembly/reaction container, the holder may also be configured to have a "clam shell"-type structure. In such embodiments, the holder circumference would typically comprise or open along a vertical seam and further comprise one or more vertical hinges (e.g., opposite the seam). The vertical seam may also include a locking mechanism. Thus, in one embodiment, a reactor system may include a holder comprising one or more vertical seams at which the holder may be opened and/or closed and/or may further comprise one or more vertical hinges. In certain embodiments, the one or more vertical hinges may be positioned approximately opposite the one or more vertical seams. Such a format may make loading and unloading of the mobile carriage assembly simpler for the operator.

As mentioned above, the holder may comprise one or more heat transfer (e.g., heat exchange) and/or anti-swirl baffles (e.g., (9)). Such baffles may serve as "speed bumps" on the holder wall that the reaction container may wrap around without tearing yet still provide sufficient resistance to flow. Other baffles may include those described in, for example, U.S. Ser. No. 12/605,329, published as US 2011-0059523 A1 (incorporated herein by reference in its entirety). The holder (6) and/or baffle(s) may be formed of any suitable material (e.g., carbon steel, stainless steel (e.g., 304, 304L, 316, 316L, 317, 317L, AL6XN), aluminum, Inconel® (e.g., Inconel 625, Chronin 625, Altemp 625, Haynes 625, Nickelvac 625 and Nicrofer 6020), Incoloy®, Hastelloy (e.g., A, B, B2, B3, B142T, Hybrid-BC1, C, C4, C22, C22HS, C2000, C263, C276, D, G, G2, G3, G30, G50, H9M, N, R235, S, W, X), Monel®, titanium, Carpenter 20®, plastic, rubber, and/or mixtures of such materials. The baffle may be incorporated into, attached or affixed to a reaction vessel (e.g., holder (6)) by any suitable method provides provided that method provides a substantially seamless attachment point (e.g., a seamless joint or boundary between materials) to provide a surface that may be simply and efficiently sanitized. A "substantially seamless attachment point", "seamless joint", or "crevice-free joint" typically indicates that the boundary between the baffle and the reaction vessel is substantially undetectable by either visual and/or other means (e.g., microscopy). It may also indicate that the boundary does not retain any residue from prior reactions following a standard cleaning procedure typically used by the skilled artisan to "sanitize" such equipment. The system is therefore suitable for sanitization using industry-accepted "clean-in-place" and "sterilize-in-place" systems using any suitable cleaning agent including but not limited to detergents, brushes, and/or steam. Such a boundary affords itself to simple and efficient sanitization, as defined below. Other types of baffles, materials, and the like may also be suitable as would be understood by one of ordinary skill in the art.

All documents cited or referred to herein are hereby incorporated by reference in their entirety into this description. While the description provided herein may be presented in terms of the preferred embodiments, it is understood that variations and modifications will occur to those skilled in the art. Therefore, it is intended that the appended claims cover all such equivalent variations that come within the scope of the claimed subject matter.

What is claimed is:

1. A reactor system comprising a mobile carriage assembly and a mobile carriage holder, wherein:
   the mobile carriage assembly comprises:
      at least one wheel or track for fixably attaching the mobile carriage assembly to the holder; and,
      a disposable reaction container reversibly attached thereto and comprising a sterile, sealable interior chamber; and,
   the mobile carriage holder comprises a receiving implement for receiving the mobile carriage assembly, an interior, and a door;
   wherein:
      the interior of the holder maintains the desire geometry of the disposable reaction container; and,
      the door of the holder contains the disposable reaction container in the interior of the holder.

2. The reactor system of claim 1 wherein the mobile carriage holder comprises a heat transfer jacket.

3. The reactor system of claim 1 wherein the mobile carriage assembly is fixably attached to the mobile carriage holder.

4. The reactor system of claim 3 wherein the mobile carriage holder comprises a heat transfer jacket.

5. The reactor system of claim 3 further comprising an impellar positioned within the sterile, sealable interior chamber of the disposable reaction container.

6. The reactor system of claim 5 wherein the mobile carriage assembly holder further comprises at least one anti-swirl and/or heat transfer baffle.

7. The reactor system of claim 6 wherein the disposable reaction container comprises reaction components, wherein the reaction components are for a reaction selected from the group consisting of a chemical process, a pharmaceutical process, and a biological process, and wherein the biological process is selected from the group consisting of microbiological culture, mammalian cell culture, and plant cell culture.

8. The reactor system of claim 1 wherein the mobile carriage assembly is reversibly attached to the mobile carriage holder.

9. The reactor system of claim 8 wherein the mobile carriage holder comprises a heat transfer jacket.

10. The reactor system of claim 8 further comprising an impellar positioned within the sterile, sealable interior chamber of the disposable reaction container.

11. The reactor system of claim 10 wherein the mobile carriage assembly holder further comprises at least one anti-swirl and/or heat transfer baffle.

12. A method for carrying out a reaction using a reactor system of claim 11, wherein the reaction is selected from the group consisting of a chemical process, a pharmaceutical process, and a biological process, and wherein said biological process is selected from the group consisting of microbiological culture, mammalian cell culture, and plant cell culture.

13. The reactor system of claim 1 wherein the mobile carriage assembly is fixably and reversibly attached to the mobile carriage holder.

14. The reactor system of claim 13 wherein the mobile carriage holder comprises a heat transfer jacket.

15. The reactor system of claim 1 further comprising an impellar positioned within the sterile, sealable interior chamber of the disposable reaction container.

16. The reactor system of claim 15 wherein the mobile carriage assembly holder further comprises at least one anti-swirl and/or heat transfer baffle.

17. The reactor system of claim 16 wherein the disposable reaction container comprises reaction components, wherein the reaction components are for a reaction selected from the group consisting of a chemical process, a pharmaceutical process, and a biological process, and wherein the biological process is selected from the group consisting of microbiological culture, mammalian cell culture, and plant cell culture.

18. The reactor system of claim 1 wherein the mobile carriage assembly holder further comprises at least one anti-swirl and/or heat transfer baffle.

19. The reactor system of claim 1 wherein the disposable reaction container comprises reaction components, wherein the reaction components are for a reaction selected from the group consisting of a chemical process, a pharmaceutical process, and a biological process, and wherein the biological process is selected from the group consisting of microbiological culture, mammalian cell culture, and plant cell culture.

20. A method for carrying out a reaction using a reactor system of claim 1, wherein the reaction is selected from the group consisting of a chemical process, a pharmaceutical process, and a biological process, and wherein said biological process is selected from the group consisting of microbiological culture, mammalian cell culture, and plant cell culture.

21. The reactor system of claim 1 wherein the receiving implement comprises one or more wheels or tracks.

22. A method for carrying out a reaction using a reactor system of claim 21, wherein the reaction is selected from the group consisting of a chemical process, a pharmaceutical process, and a biological process, and wherein said biological process is selected from the group consisting of microbiological culture, mammalian cell culture, and plant cell culture.

* * * * *